US007235053B2

(12) United States Patent
Phillips

(10) Patent No.: US 7,235,053 B2
(45) Date of Patent: Jun. 26, 2007

(54) METHOD AND APPARATUS FOR DETERMINING BLOOD FLOW CHARACTERISTICS IN SMALL INFANTS

(75) Inventor: Robert Allan Phillips, Coffs Harbour (AU)

(73) Assignee: USCOM Limited, Sydney (AU)

( * ) Notice: Subject to any disclaimer, the term of this patent is extended or adjusted under 35 U.S.C. 154(b) by 152 days.

(21) Appl. No.: 10/760,867

(22) Filed: Jan. 20, 2004

(65) Prior Publication Data

US 2005/0159664 A1    Jul. 21, 2005

(51) Int. Cl.
  *A61B 5/02*   (2006.01)
(52) U.S. Cl. .................................................. 600/508
(58) Field of Classification Search ............. 600/450, 600/453–455, 481, 508, 459, 462, 467, 468, 600/526, 485
See application file for complete search history.

(56) References Cited

U.S. PATENT DOCUMENTS

| | | | | |
|---|---|---|---|---|
| 4,562,843 | A | * | 1/1986 | Djordjevich et al. ........ 600/485 |
| 4,796,634 | A | | 1/1989 | Huntsman et al. |
| 5,052,395 | A | | 10/1991 | Burton et al. |
| 5,103,828 | A | * | 4/1992 | Sramek ...................... 600/481 |
| 6,565,513 | B1 | | 5/2003 | Phillips |

OTHER PUBLICATIONS

Munk, Anja et al. "Diameter of the Infrarenal Aorta and the Iliac Arteries in Children: Ultrasound Measurements" Transplantation Feb. 27, 2002 vol. 73, No. 4, pp. 631-635.

* cited by examiner

*Primary Examiner*—George Manuel
(74) *Attorney, Agent, or Firm*—Merchant & Gould P.C.

(57) ABSTRACT

A method of determining the cardiac output of an infant, the method comprising the steps of: (a) measuring the infant's weight; (b) measuring the velocity time integral and stroke distance of blood flowing from the heart of the patient; and (c) utilizing the two measurement in step (a) and step (b) to determine the cardiac output of the infant.

21 Claims, 6 Drawing Sheets

METHOD AND APPARATUS FOR DETERMINING BLOOD FLOW CHARACTERISTICS IN SMALL INFANTS

FIELD OF THE INVENTION

The present invention relates to the measurement of cardiac output of infants including pre-term infants and foetuses.

BACKGROUND OF THE INVENTION

Cardiac output and measurement of cardiac dimensions and haemodynamics are very important indicators in measuring health or detecting disease. The cardiac output, the volume of blood ejected by the heart per minute, is an essential measure of cardiac health.

Unfortunately, it is often difficult to measure actual cardiac output. Whilst normal fluid flow outputs consist of a flow velocity times a cross section area, it is often difficult to accurately measure the cross sectional area of cardiac vessels. Hence, there is often a large degree of error associated with actual cardiac measurements.

This is particularly the case with small pre-term infants and, even, foetuses. It would be desirable to be able to measure the cardiac output of such individuals.

SUMMARY OF THE INVENTION

It is an object of the present invention to provide for an improved or alternative way of measurement cardiac output in infants or the like.

In accordance with a first aspect of the present invention, there is provided a method of determining the cardiac output of an infant, the method comprising the steps of: (a) measuring the infant's weight; (b) measuring the velocity time integral and stroke distance of blood flowing from the heart of the patient; and (c) utilising the two measurement in step (a) and step (b) to determine the cardiac output of the infant.

Preferably, the method also includes the step of measuring the correlation between an infant's weight and a corresponding cross sectional area of a cardiac valve for a population of infants and utilising the correlation in step (c) to determine the cardiac output of the infant under study. Preferably, the population can be selected having similar body characteristics to the infant. The method can be utilised to determine the output from either the aortic annulus or the pulmonary annulus.

Preferably, in one instance, the method can comprise utilising the formula substantially of the form: aortic annular diameter=0.093×weight (kg)+0.25 cm to determine the diameter of the aortic annular and then determining a cross sectional area.

Preferably, in one instance, the method utilising can comprise utilising the formula substantially of the form: pulmonary annular diameter=0.1×weight (kg)+0.368 to determine the diameter of the pulmonary valve and then determining a cross sectional area.

BRIEF DESCRIPTION OF THE DRAWINGS

The preferred embodiments of the present invention will now be described with reference to the accompanying drawings in which.

DESCRIPTION OF PREFERRED AND OTHER EMBODIMENTS

In the preferred embodiment, a new method is provided for measurement of cardiac output in small infants through the utilisation of correlations between weight measurements and integrated transvalvular haemodynamics.

More particularly, in the preferred embodiment, an infant's weight is utilised to correlate with the cross sectional area of the infant's heart in haemodynamic measurements.

Recently, in PCT application No. PCT/AU99/00507 and U.S. Pat. No. 6,565,513 entitled "Ultrasonic Cardiac Output Monitor", the contents of which are hereby incorporated by cross reference, a system was proposed for the continuous wave Doppler direct measurement of transvalvular cardiac flows. Such a system can readily be adapted for use with the preferred embodiment of the present invention to measure flow outputs in infants.

Figure 1:
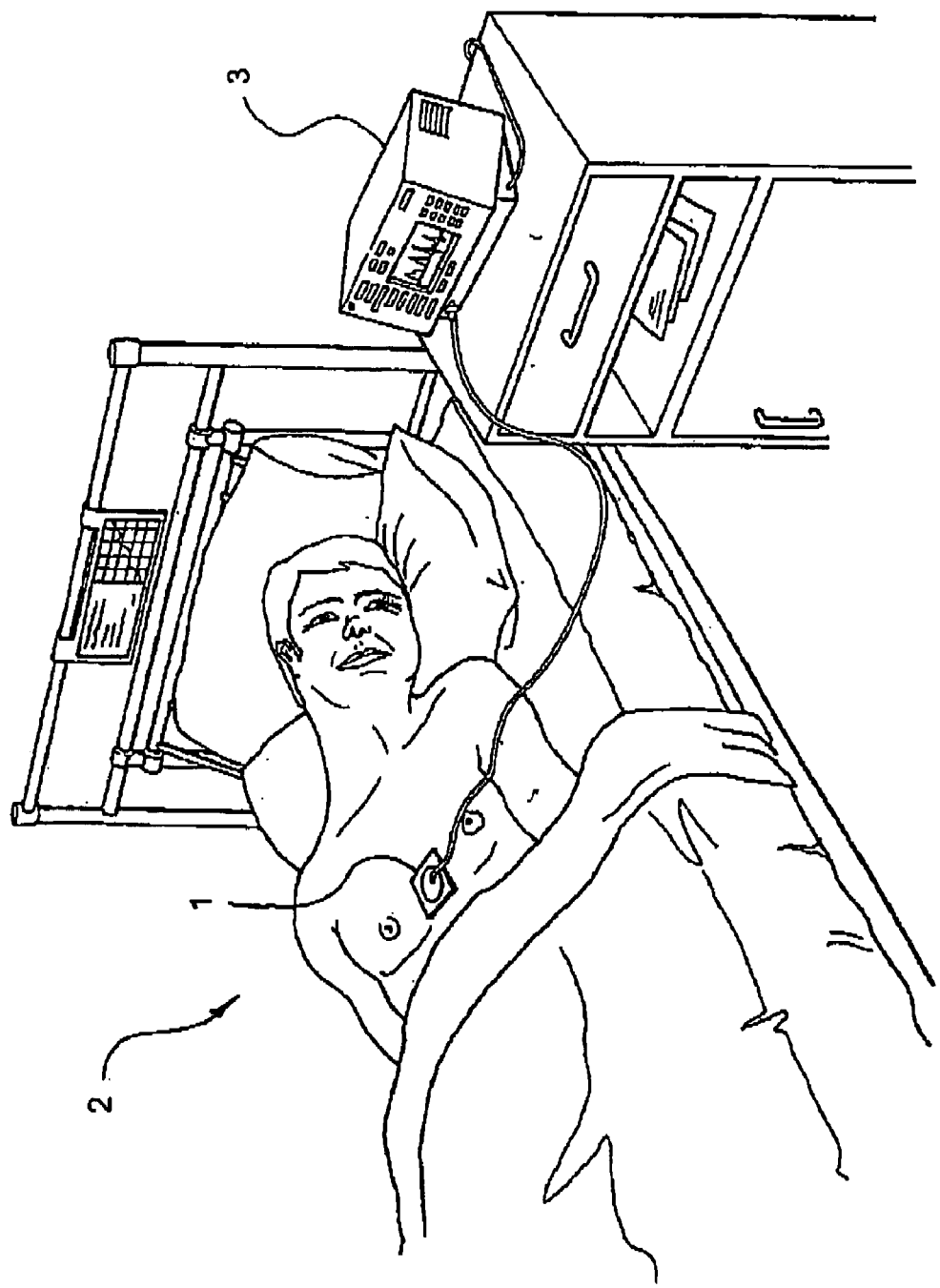
FIG. 1 is a side perspective view of cardiac monitoring of an adult.

FIG. 1 illustrates the system described in the aforementioned patent specification wherein an ultrasonic transducer device 1 is interconnected to a small processing computer 3 and utilised to monitor blood flows within the heart of patient 2.

Figure 2:
FIG. 2 illustrates the cardiac monitoring of a neonatal infant.

The preferred embodiment is particularly directed to young infants such as those born prematurely. Turning now to FIG. 2, there is illustrated the adaptation of the interconnection of the transducer device to an infant 5. In this case, the infant 5 has the transducer device 6 interconnect to the infant's chest so as to provide for Continuous CW ultrasonic monitoring of blood flows.

Figure 3:
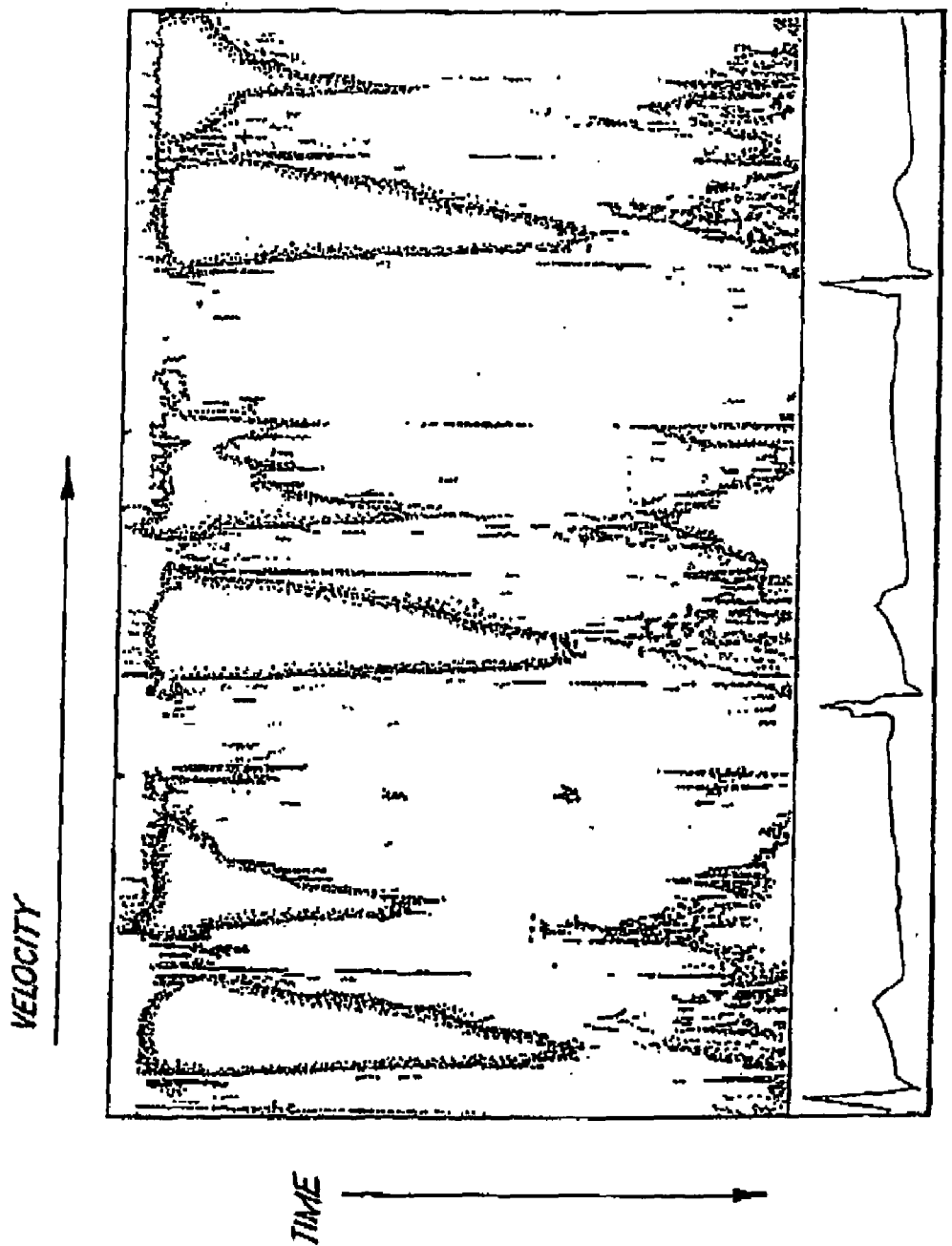
FIG. 3 illustrates an example cardiac output.
Figure 4:
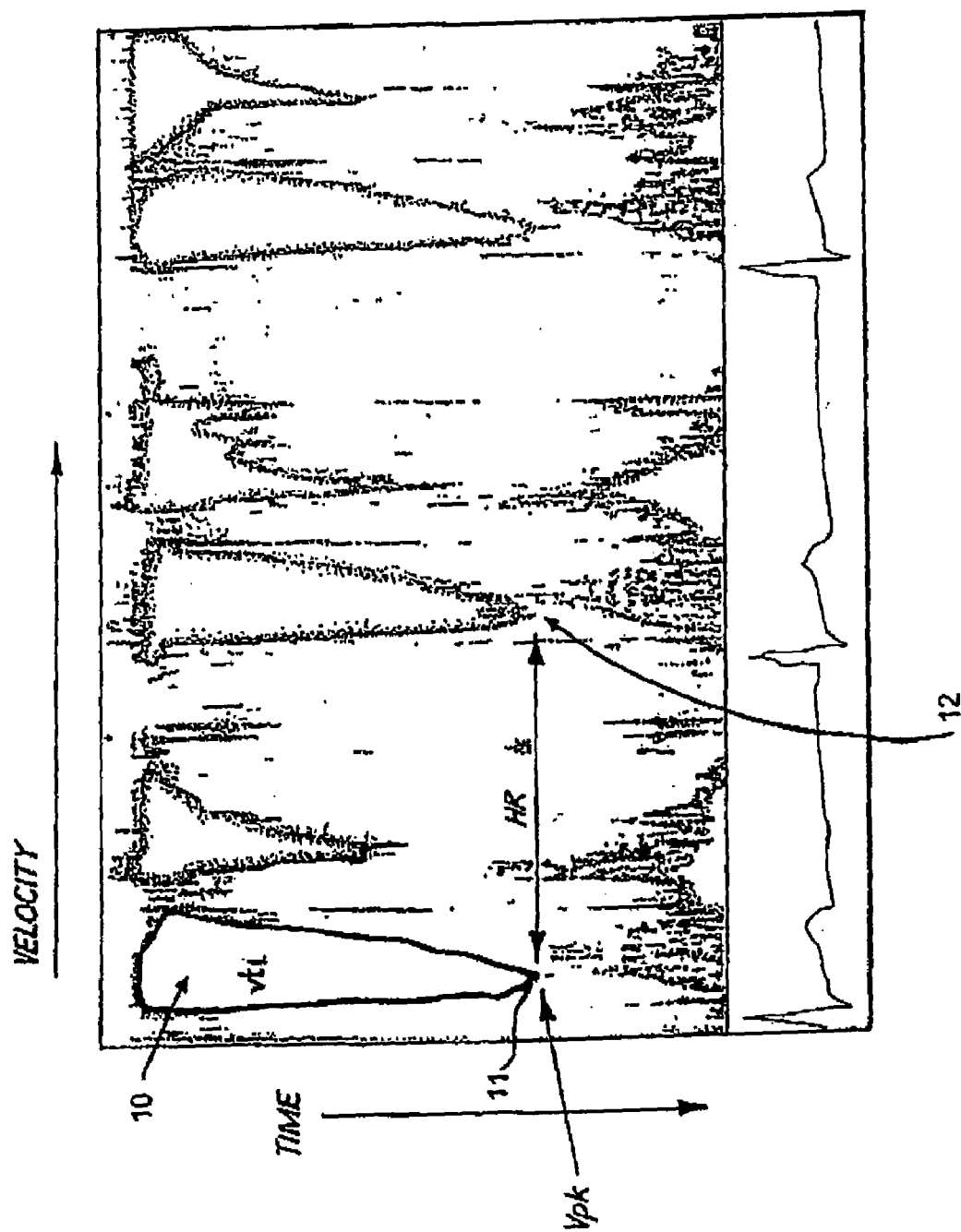
FIG. 4 illustrates an analysis of the cardiac output of FIG. 3.

Turning to FIG. 3, there is illustrated a typical screen dump from an ultrasonic transducer device being placed in accordance with the teaching of the aforementioned application so as to measure transvalvular flows. In FIG. 4, there is illustrated an analysis of the image of FIG. 3. With such an output, cardiac output (CO) can be calculated by measurement of the Doppler spectral flow profile of the image of FIG. 3 to determine the area under the curve or the velocity time integral (vti) or stroke distance—the distance a single red blood cell travels per beat. In FIG. 4, there is illustrated the vti 10 which is an "area under the curve" measurement. Further, the heart rate can be determining from the spectral flow profile as the time between peaks e.g. 11, 12.

From a measurement of the cross sectional area of the flow (XSA), it is possible to determine the stroke volume (SV) by multiplying the vti so that SV=vti×XSA. SV is the volume of blood ejected by the heart per beat in $cm^3$. CO is a function of SV and heart rate (HR), or the volume per beat times the number of beats per minute, so CO=SV×HR in litres per minute.

The values for these formulae can be derived from direct measurement of the Doppler flow profile of FIG. 3 and FIG. 4, with the exception of the flow cross sectional area.

One possibility for measuring the flow cross-sectional area is to measure the flow diameter using two-dimensional ultrasound, and calculating the XSA using $\pi r^2$. However, normal values for flow diameters obtained are in the order of 1.5 to 2.5 cm for adults and 0.5 cm for term neonates. The resolution of 2D B-Mode ultrasound at 3 Mhz is approximately 1 mm or about 5%. This 5% linear error is the best possible result and, if 95% confidence intervals define sensitivity and equal two standard deviations then the error is approximately 10%. If this error is squared when applied to the $\pi r^2$ formula to determine XSA, the resulting potential error in measurement of the cardiac output is approximately 21%. For neonates lower frequency ultrasound can be used, say 7.5 Mhz with a corresponding increase in spatial resolution, however as the subject diameter is also much smaller, say 0.5 cm in term neonates, the % errors remain similar.

It will be noted that the error associated with measurement of the Doppler functions alone for application of these haemodynamics equations is less than 5%. The figures for sensitivity of Doppler echo detection of changes in CO are reflected in clinical data.

In the preferred embodiment, a more accurate method of measuring flow diameter is utilised to provide an increase in the sensitivity of Doppler ultrasound to detection of changes in cardiac output and to thereby improve the clinical usefulness of Doppler flow measurements in infants.

CO measurements are generally made from Doppler flow profiles across the aortic and pulmonary valves. However, it is also possible to determine CO from the flow across the mitral and tricuspid valves. Measurement of Aortic annular diameter, the two dimensional measure from which the XSA is derived, can generally be performed with reasonable accuracy because the arterial walls are normally perpendicular to insonation in the parasternal long axis position, resulting in high levels of reflected signals. Measurement of the pulmonary annular diameter is more problematic because the vessel walls are often parallel to the ultrasound beam and reflected signal less intense. Of additional importance, the pulmonary artery is the most accessible flow signal for Doppler measurement of CO.

In the development of the preferred embodiment, a series of studies were conducted of cardiac output of neonates and a correlation determined between the weight of the neonate and the corresponding pulmonary artery annular diameter. In the study, 978 pre-term infants were measured 20 to 30 wks gestational age, 0.420 to 1.690 kg Mean values: Weight=0.986±0.269 kg, PV=0.507±0.059 cm r=0.649, p<0.000 Regression: PV=0.1 wt(kg)+0.368 cm.

Figure 5:
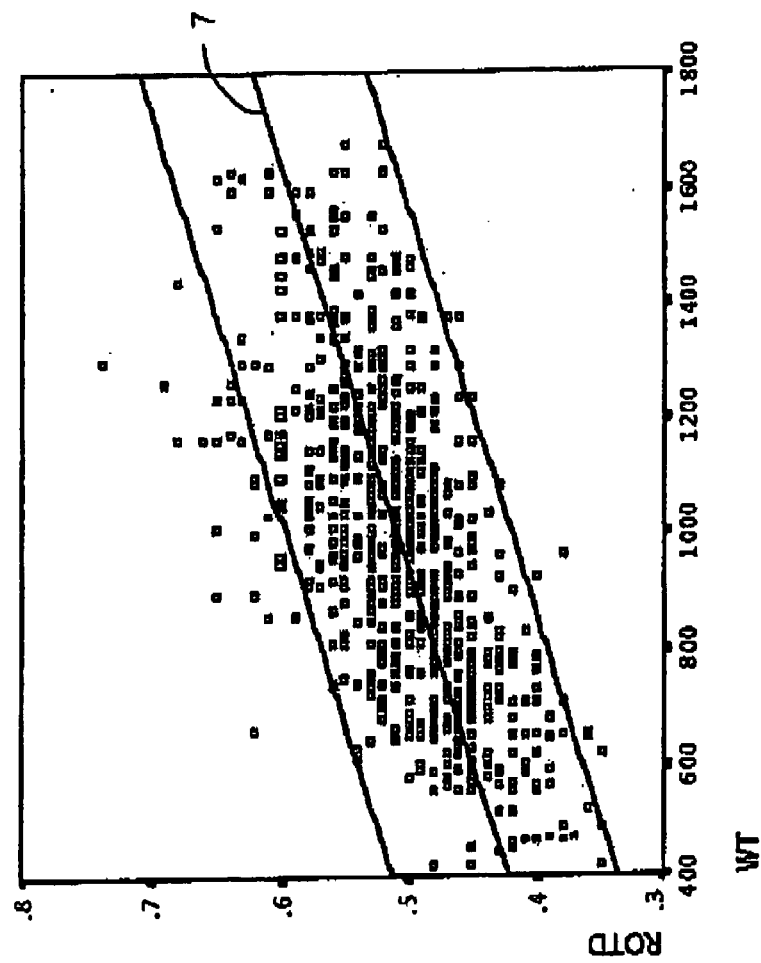
FIG. 5 is an example plot of weight to ventricular diameter measurements in infants.

Turing to FIG. 5, there is illustrated a plot of weight versus pulmonary artery annular diameter. The regression line 7 was subsequently derived utilising standard techniques.

Weight has the additional benefits of being a non-derived unit, is easily measured in infants, and is a commonly patient informed value. Through subsequent analysis, it has been found that the size of the aortic annular diameter can be approximately described by the regression equation as AV=0.093 wt (kg)+0.343 cm. If the heart grows in unison and at a predictable rate, then the pulmonary artery annular diameter will show constant a relationship to the aortic annulus in infants. Hence, the Cardiac Output can be predicted using the aortic annular diameter regression equation and integrated haemodynamics. As input CO equals output CO in the absence of shunt or significant regurgitation, a weight referenced equation to predict the pulmonary artery annular diameter can also be utilised. This can then be applied to standard haemodynamics to determine flow XSA, SV and CO.

Figure 6:
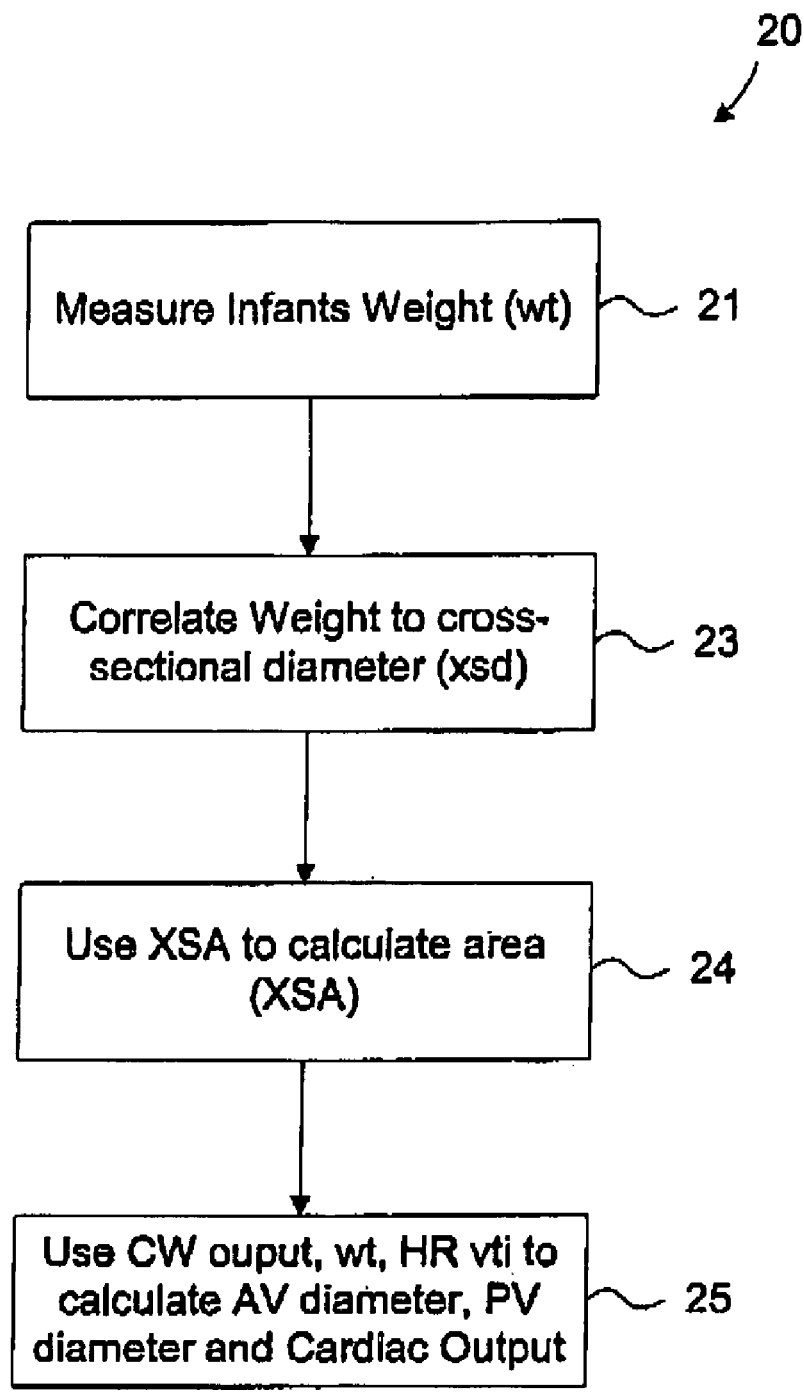
FIG. 6 illustrates a flowchart of the steps of the preferred embodiment.

FIG. 6 therefore illustrates a flowchart of the steps involved in the preferred embodiment. Firstly, the weight of the infant is determined 21. Next, from the output screen dump of the transducer monitoring device, the heart rate is determined and the velocity time integral is measured 23. These parameters are then utilised to calculate the corresponding AV and PV diameter which can then be utilised to calculate the cardiac output.

In a first initial embodiment a measure for a population of individuals was studied and derived vti values of children and adults found in a sample population to be: Pvti=20.76±3.36 cm and Avti=23.38±3.38 cm, with a vti PV:AV ratio of 1:1.126.

Whilst the above values were used in calculations, obviously other population samples could be utilised.

As CO=TO×HR×vti, and pulmonary flow equals systemic (aortic) flow in the absence of a shunt or significant regurgitation, then $$PV\ XSA \times HR \times PVvti = AV\ XSA \times HR \times AVvti$$

As $XSA=\pi r^2$ and AV diameter=(0.093×wt+0.343) and AV radius=(0.093×wt+0.343)/2 then $$(\pi \times (PVd/2)^2) \times 20.76 \times HR = (\pi \times ((0.093 \times wt+0.343)/2)^2) \times 23.38 \times HR$$

If HR PV=HR AV then $$(\pi \times (PVd/2)^2) \times 20.76 = (\pi \times ((0.093 \times wt+0.343)/2)^2) \times 23.38/20.76$$

$$(\pi \times (PVd/2)^2) = (\pi \times ((0.093 \times wt+0.343)/2)^2) \times 23.38/20.76$$

$$\pi \times (PVd/2)^2 = \pi \times ((0.093 \times wt+0.343)/2)^2 \times 1.126/\pi$$

$$(PVd/2)^2 = ((0.093 \times wt+0.343)/2)^2 \times 1.126$$

Taking the square root of both sides implies:

$$\sqrt{(PVd/2)^2} = \sqrt{((0.093 \times wt+0.343)/2)^2} \times \sqrt{1.126}$$

$$PVd/2 = (0.093 \times wt+0.343)/2 \times 1.06$$

$$PVd/2 = (0.093 \times wt+0.343) \times 1.06/2$$

Then PV Radius=PVd/2=(0.093×wt+0.343)×0.53=0.04929×wt+0.18179 and PV diameter=PVd/2×2=(0.093×wt+0.343)×1.06=0.09858×wt+0.36358

Therefore both the aortic annular and the pulmonary annular diameter can be determined from simple weight measurements as $$AVd=0.093 \times wt+0.343$$

and $$PVd=0.1 \times wt+0.363$$

As a result, the above formulas can be utilised to calculate the cross-sectional area of the aortic and pulmonary valves. From this calculation, the stroke volume and CO can also be determined.

The flow cross sectional area, XSA, in $cm^2$ is required to calculate flow volumes and can be determined from direct 2D measurements or calculated from height referenced algorithms. From the above, the XSA algorithms are:

Aortic

As $AVd=0.093 \times wt+0.343$

Pulmonary $$PVd=0.1 \times wt+0.368$$

then $PV\ XSA=\pi((0.1 \times wt)+0.368)/2)^2$

Stroke Volume

Stroke volume, in cm³, is the volume of blood ejected from the heart per beat and is equal to the cross sectional area times the flow vti. Therefore:

$$SV\ AV\ (\text{adult+children}) = \pi((0.093 \times wt + 0.343)/2)^2 \times AVvti$$

$$SV\ PV\ (\text{adult+children}) = \pi((0.1 \times wt + 0.363)/2)^2 \times PVvti$$

Cardiac Output

Cardiac output, in litres per minute, is the volume of blood ejected from the heart per minute and is a function of the cross sectional area, the flow vti and the heart rate.

$$CO\ AV\ (\text{adult+children}) = \pi((0.093 \times wt + 0.343)/2)^2 \times AVvti \times HR$$

$$CO\ PV\ (\text{adult+children}) = \pi((0.1 \times wt + 0.363)2)^2 \times PVvti \times HR$$

By using the above formulas, a determination of important cardiac morphologic dimensions can be made from an infant measurement. This measurement provides an alternative to the currently practiced direct measurement of these dimensions using complex imaging. This can allow for stand alone Doppler instruments to determine accurate measures of cardiac function without the use of complex and expensive imaging devices. This results in an improved method of determining CO in echocardiographic practice.

The preferred embodiment can also be utilized to determine the cardiac output of a foetus through the measurement of the foetus' cardiac parameters through the wall of the womb and the estimation of the foetus' weight from measuring the volume of space occupied by the foetus and performing an approximation to the weight of the foetus composition.

The foregoing describes preferred embodiments of the present invention. Modifications, obvious to those skilled in the art can be made there to without departing from the scope of the invention.

I claim:

1. A method of determining the cardiac output of an infant, the method comprising the steps of:
   (a) measuring the infant's weight;
   (b) measuring the velocity time integral and stroke distance of blood flowing through a cardiac valve of the heart of the infant; and
   (c) calculating on the basis of the measurements in step (a) and step (b) the cardiac output of the infant.

2. A method as claimed in claim 1 further comprising the step of measuring the correlation between an infant's weight and the cross sectional area of a cardiac valve of a population of infants and utilising the correlation in step (c) to determine the cardiac output of the infant.

3. A method as claimed in claim 2 wherein said population is selected having similar body characteristics to said infant.

4. A method as claimed in claim 1 wherein said method is utilised to determine the output from either the aortic annulus or the pulmonary annulus.

5. A method as claimed in claim 1 wherein said step of calculating comprises utilising the formula substantially of the form:

pulmonary annular diameter=0.1×weight(kg)×0.368 to determine the diameter of the pulmonary valve and then determining a cross sectional area.

6. A method as claimed in claim 1 wherein the step (b) includes measuring the velocity time integral and stroke distance of blood flowing immediately downstream of the cardiac valve.

7. A method as claimed in claim 1 wherein the step (b) includes measuring the velocity time integral and stroke distance of blood flowing within the ascending aorta.

8. A method of determining the cardiac output of an infant, the method comprising the steps of:
   (a) measuring the infant's weight;
   (b) measuring the velocity time integral and stroke distance of blood flowing from a cardiac valve of the heart of the infant; utilising the formula substantially of the form:

aortic annular diameter=0.093×weight(kg)+0.25 cm to determine the diameter of the aortic annular and then determining a cross sectional area; and
   (c) calculating on the basis of the two measurements in step (a) and step (b) the cardiac output of the infant.

9. A method of determining the cardiac output of a foetus, the method comprising the steps of:
   (a) estimating the foetus' weight;
   (b) measuring the velocity time integral and stroke distance of blood flowing through a cardiac valve of the heart of the foetus; and
   (c) calculating on the basis of the measurements in step (a) and step (b) the cardiac output of the prenatal foetus.

10. A method as claimed in claim 9 wherein the step (b) includes measuring the velocity time integral and stroke distance of blood flowing immediately downstream of the cardiac valve.

11. A method as claimed in claim 9 wherein the step (b) includes measuring the velocity time integral and stroke distance of blood flowing within the ascending aorta.

12. A method as claimed in claim 9 wherein said method is utilised to determine the output from either an aortic annulus or a pulmonary annulus of the foetus.

13. A method as claimed in claim 9 wherein the step (c) includes utilising the formula substantially of the form:

aortic annular diameter=0.093×weight (kg)+0.25 cm to determine a diameter of an aortic annular of the foetus and then determining a cross sectional area of the aortic annular.

14. A method of determining the cardiac output of an infant, the method comprising the steps of:
   (a) measuring the infant's weight;
   (b) measuring the velocity time integral and stroke distance of blood flowing at a cardiac valve of the heart of the infant; and
   (c) calculating on the basis of the measurements in step (a) and step (b) the cardiac output of the infant.

15. A method as claimed in claim 14 further comprising the step of measuring the correlation between an infant's weight and the cross sectional area of a cardiac valve of a population of infants and utilising the correlation in step (c) to determine the cardiac output of the infant.

16. A method as claimed in claim 15 wherein said population is selected having similar body characteristics to said infant.

17. A method as claimed in claim 14 wherein said method is utilised to determine the output from either the aortic annulus or the pulmonary annulus.

18. A method as claimed in claim 14 wherein said step of utilising comprises utilising the formula substantially of the form:

$$\text{pulmonary annular diameter} = 0.1 \times \text{weight(kg)} + 0.368$$

to determine the diameter of the pulmonary valve and then determining a cross sectional area.

19. A method as claimed in claim 14 wherein the step (c) includes utilising the formula substantially of the form:

$$\text{aortic annular diameter} = 0.093 \times \text{weight (kg)} + 0.25 \text{ cm}$$

to determine a diameter of an aortic annular of the foetus and then determining a cross sectional area of the aortic annular.

20. A method as claimed in claim 14 wherein the step (b) includes measuring the velocity time integral and stroke distance of blood flowing immediately downstream of the cardiac valve.

21. A method as claimed in claim 14 wherein the step (b) includes measuring the velocity time integral and stroke distance of blood flowing within the ascending aorta.

* * * * *